US008227649B2

United States Patent
Nappa et al.

(10) Patent No.: US 8,227,649 B2
(45) Date of Patent: *Jul. 24, 2012

(54) CATALYSTS AND PROCESS TO MANUFACTURE 2,3,3,3-TETRAFLUOROPROPENE

(75) Inventors: Mario Joseph Nappa, Newark, DE (US); Andrew Jackson, Newark, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/188,787

(22) Filed: Jul. 22, 2011

(65) Prior Publication Data

US 2011/0282112 A1    Nov. 17, 2011

Related U.S. Application Data

(63) Continuation of application No. 12/792,969, filed on Jun. 3, 2010, now Pat. No. 7,985,884.

(60) Provisional application No. 61/193,674, filed on Jun. 3, 2009, provisional application No. 61/256,341, filed on Oct. 30, 2009.

(51) Int. Cl.
   *C07C 17/00* (2006.01)
(52) U.S. Cl. ...................................................... 570/157
(58) Field of Classification Search ................... 570/157
   See application file for complete search history.

(56) References Cited

U.S. PATENT DOCUMENTS

| 3,413,363 | A  |   | 11/1968 | Pindzola |
| 6,034,289 | A  | * | 3/2000  | Christoph et al. ............ 570/156 |
| 7,423,188 | B2 |   | 9/2008  | Miller et al. |
| 7,476,771 | B2 |   | 1/2009  | Miller et al. |
| 7,560,602 | B2 | * | 7/2009  | Van Der Puy et al. ........ 570/156 |
| 2006/0106263 | A1 |   | 5/2006 | Miller et al. |

FOREIGN PATENT DOCUMENTS

| WO | 2007056194 A1 | 5/2007 |
| WO | 2008002501 A2 | 1/2008 |
| WO | 2008008350 A2 | 1/2008 |
| WO | WO 2009/003157 A1 * | 12/2008 |

OTHER PUBLICATIONS

PCT/US2010/037179 International Search Report, Nov. 22, 2010.

* cited by examiner

*Primary Examiner* — Jafar Parsa

(57) ABSTRACT

Disclosed is a process for the manufacture of 2,3,3,3-tetrafluoropropene comprising: (a) contacting 1,1,1,2,3-pentafluoropropane with a catalyst comprised of chromium (III) oxide and from 0.1% to 2% of an alkali metal disposed on the surface of said catalyst, to produce a product mixture comprising 2,3,3,3-tetrafluoropropene and hydrogen fluoride; and (b) recovering said 2,3,3,3-tetrafluoropropene from the product mixture produced in (a).

18 Claims, No Drawings

US 8,227,649 B2

CATALYSTS AND PROCESS TO MANUFACTURE 2,3,3,3-TETRAFLUOROPROPENE

CROSS REFERENCE TO RELATED APPLICATIONS

This application is a continuation of U.S. application Ser. No. 12/792,969, filed Jun. 3, 2010, which claims priority to U.S. Provisional application 61/183,674, filed Jun. 3, 2009 and U.S. Provisional application 61/256,341, filed Oct. 30, 2009.

BACKGROUND INFORMATION

1. Field of the Disclosure

This disclosure relates in general to methods of synthesis of fluorinated olefins.

2. Description of the Related Art

The fluorocarbon industry has been working for the past few decades to find replacement refrigerants for the ozone depleting chlorofluorocarbons (CFCs) and hydrochlorofluorocarbons (HCFCs) being phased out as a result of the Montreal Protocol. The solution for many applications has been the commercialization of hydrofluorocarbon (HFC) compounds for use as refrigerants, solvents, fire extinguishing agents, blowing agents and propellants. These new compounds, such as HFC refrigerants, HFC-134a and HFC-125 being the most widely used at this time, have zero ozone depletion potential and thus are not affected by the current regulatory phase-out as a result of the Montreal Protocol.

In addition to ozone depleting concerns, global warming is another environmental concern in many of these applications. Thus, there is a need for compositions that meet both low ozone depletion standards as well as having low global warming potentials. Certain hydrofluoroolefins are believed to meet both goals. Thus there is a need for manufacturing processes that provide halogenated hydrocarbons and fluoroolefins that contain no chlorine that also have a low global warming potential. There is also considerable interest in developing new refrigerants with reduced global warming potential for the mobile air-conditioning market.

HFC-1234yf ($CF_3CF=CH_2$) and HFC-1234ze ($CF_3CH=CHF$), both having zero ozone depletion and low global warming potential, have been identified as potential refrigerants. U.S. Patent Publication No. 2006/0106263 A1 discloses the production of HFC-1234yf by a catalytic vapor phase dehydrofluorination of $CF_3CF_2CH_3$ or $CF_3CHFCH_2F$, and of HFC-1234ze (mixture of E- and Z-isomers) by a catalytic vapor phase dehydrofluorination of $CF_3CH_2CHF_2$.

There is a continuing need for more selective and efficient manufacturing processes for the production of HFC-1234yf

SUMMARY

In one aspect, disclosed is a process for the manufacture of 2,3,3,3-tetrafluoropropene comprising: contacting 1,1,1,2,3-pentafluoropropane with a catalyst comprised of chromium (III) oxide and from 0.1% to 2% of an alkali metal disposed on the surface of said catalyst, to produce a product mixture comprising 2,3,3,3-tetrafluoropropene and hydrogen fluoride; and recovering said 2,3,3,3-tetrafluoropropene from the product mixture produced above.

In another aspect, disclosed is a process for the manufacture of 2,3,3,3-tetrafluoropropene comprising: contacting 1,1,1,2,3-pentafluoropropane with a catalyst comprised of chromium (III) oxide and from 0.5% to 2.0% of an alkali metal dispersed throughout the particles of said catalyst, to produce a product mixture comprising 2,3,3,3-tetrafluoropropene and hydrogen fluoride; and recovering said 2,3,3,3-tetrafluoropropene from the product mixture produced above.

The foregoing general description and the following detailed description are exemplary and explanatory only and are not restrictive of the invention, as defined in the appended claims.

DETAILED DESCRIPTION

In one aspect, disclosed is a process for the manufacture of 2,3,3,3-tetrafluoropropene comprising: dehydrofluorinating 1,1,1,2,3-pentafluoropropane in the presence of a dehydrofluorination catalyst comprised of chromium (III) oxide, and alkali metal, to produce a product mixture comprising 2,3,3,3-tetrafluoropropene; and recovering said 2,3,3,3-tetrafluoropropene from the product mixture produced in the dehydrofluorination. In one embodiment, the product mixture comprising 2,3,3,3-tetrafluoropropene further comprises less than 20 parts per hundred on a molar basis of 1,1,1,2,2-pentafluoropropane. In another embodiment, the product mixture comprising 2,3,3,3-tetrafluoropropene further comprises less than 10 parts per hundred on a molar basis of 1,1,1,2,2-pentafluoropropane. In one embodiment, the dehydrofluorination catalyst comprises chromium (III) oxide and at least 1000 ppm alkali metal. In another embodiment, the dehydrofluorination catalyst comprises chromium (III) oxide and at least 3000 ppm alkali metal. In yet another embodiment, the dehydrofluorination catalyst comprises chromium oxide and at least 5000 ppm alkali metal. In yet another embodiment, the dehydrofluorination catalyst comprises chromium oxide and at least 1000 ppm potassium. In yet another embodiment, In another embodiment, the dehydrofluorination catalyst comprises from 0.1% to 3% boron and at least 3000 ppm of alkali metal. In another embodiment, the dehydrofluorination catalyst comprises from 0.5% to 2% boron and at least 3000 ppm of alkali metal. In yet another embodiment, the dehydrofluorination catalyst comprises from 0.5% to 2% boron and at least 3000 ppm of sodium. In yet another embodiment, the dehydrofluorination catalyst comprises from 0.5% to 2% boron and at least 2000 ppm of potassium.

Many aspects and embodiments have been described above and are merely exemplary and not limiting. After reading this specification, skilled artisans appreciate that other aspects and embodiments are possible without departing from the scope of the invention.

Other features and benefits of any one or more of the embodiments will be apparent from the following detailed description, and from the claims Before addressing details of embodiments described below, some terms are defined or clarified.

The catalytic dehydrofluorination of hydrofluorocarbons to produce hydrofluoroolefins is ordinarily carried out in the vapor phase using a dehydrofluorination catalyst. Vapor phase dehydrofluorination catalysts are well known in the art. These catalysts include, but are not limited to, alumina, aluminum fluoride, fluorided alumina, metal compounds on aluminum fluoride, metal compounds on fluorided alumina; chromium oxides, fluorided chromium oxides, and cubic chromium trifluoride; oxides, fluorides, and oxyfluorides of magnesium, zinc and mixtures of magnesium and zinc and/or aluminum; lanthanum oxide and fluorided lanthanum oxide; carbon, acid-washed carbon, activated carbon, three dimensional matrix carbonaceous materials; and metal compounds supported on carbon. The metal compounds are oxides, fluorides, and oxyfluorides of at least one metal selected from the group consisting of sodium, potassium, rubidium, cesium, yttrium, lanthanum, cerium, praseodymium, neodymium, samarium, chromium, iron, cobalt, rhodium, nickel, copper, zinc, and mixtures thereof.

In the preparation of HFC-1234yf by dehydrofluorination of $CF_3CHFCH_2F$, it is possible to obtain either HFC-1234yf or HFC-1234ze, depending on which pair of adjacent fluorine and hydrogen atoms are eliminated. Generally, HFC-1234yf is the predominant product, although depending on reaction conditions, yields of HFC-1234ze can be as much 10 pph or more compared to HFC-1234yf. It has also been found that another by-product of the catalytic dehydrofluorination of $CF_3CHFCH_2F$ (HFC-245cb) is $CF_3CF_2CH_3$ (HFC-245cb) which can be very difficult to separate from HFC-1234yf. This product is believed to arise via the re-addition of hydrogen fluoride to HFC-1234yf in the direction opposite to that it was eliminated by. Although HFC-245cb can be catalytically dehydrofluorinated to HFC-1234yf, in practice the dehydrofluorination of HFC-245cb requires higher temperatures and a different catalyst. Depending upon the catalyst and reaction conditions, the amount of HFC-245cb produced by isomerization can be as much as from 30 to 60 parts per hundred of HFC-1234yf, resulting in significant yield losses. Selectivity for the production of HFC-1234yf can be expressed as parts per hundred of the by-product relative to the amount of HFC-1234yf. By way of example, a product mixture formed from the dehydrofluorination of HFC-245eb comprising 60% HFC-1234yf, 20% HFC-245cb and 3% HFC-1234ze would have 33 pph HFC-245cb and 5 pph HFC-1234ze.

It is possible to dehydrofluorinate $CF_3CHFCH_2F$ (HFC-245eb) to HFC-1234yf with high selectivity and very little formation of HFC-245cb using a catalyst comprising chromium (III) oxide, and alkali metal. In one embodiment, the alkali metal is at least one of sodium, potassium and cesium, or mixtures thereof.

In one embodiment, the catalyst comprises chromium (III) oxide, and an amount of alkali metal effective to produce 2,3,3,3-tetrafluoro-1-propene while producing less than 20 pph or 1,1,1,2,2-pentafluoropropane. The effective amount of alkali metal required will be dependent upon how it is distributed within the catalyst composition. The effective amount of alkali metal required is also dependent on which alkali metal is chosen. An effective amount of cesium is less than an effective amount of potassium, which is less than an effective amount of sodium.

In one embodiment, the dehydrofluorination catalyst comprises chromium (III) oxide and at least 1000 ppm alkali metal. In another embodiment, the dehydrofluorination catalyst comprises chromium (III) oxide and at least 3000 ppm alkali metal. In yet another embodiment, the dehydrofluorination catalyst comprises chromium oxide and at least 5000 ppm alkai metal. In yet another embodiment, the dehydrofluorination catalyst comprises chromium oxide and at least 1000 ppm potassium. In another embodiment, the dehydrofluorination catalyst comprises from 0.1% to 3% boron and at least 3000 ppm of alkali metal. In another embodiment, the dehydrofluorination catalyst comprises from 0.5% to 2% boron and at least 3000 ppm of alkali metal. In yet another embodiment, the dehydrofluorination catalyst comprises from 0.5% to 2% boron and at least 3000 ppm of sodium. In yet another embodiment, the catalyst comprises chromium (III) oxide, from 0.5% to 2% boron, and at least 2000 ppm potassium. In one embodiment, the catalyst is a chromium composition known as Guignet's green pigment.

In one embodiment, the dehydrofluorination catalyst may be prepared by slurrying preformed pellets or particles of chromium (III) oxide catalyst in an aqueous solution of an alkali metal salt, such as sodium carbonate, potassium carbonate or cesium carbonate. The slurry is then allowed to dry.

In another embodiment, the dehydrofluorination catalyst may be prepared by slurring chromium (III) oxide powder with an aqueous solution of an alkali metal salt, such as sodium carbonate, potassium carbonate or cesium carbonate. The slurry is then allowed to dry. In one embodiment, the dehydrofluorination catalyst is then pressed, ground into particles, and sieved to 12/20 mesh particles In yet another embodiment, the catalyst may be prepared by fusing a mixture of from 3 parts to 16 parts boric acid and 1 part potassium dichromate at from 500-800° C., cooling the mixture in air, crushing the solid to produce a powder, hydrolysis, filtering, drying, milling and screening. Numerous, examples of the preparation of Guignet's green can be found in the art, including U.S. Pat. No. 3,413,363, the disclosure of which is herein incorporated by reference.

The physical shape of the catalyst is not critical and may, for example, include pellets, powders or granules.

In one embodiment, the catalytic dehydrofluorination may be suitably conducted with the temperature set point of the reactor in the range of from about 250° C. to about 350° C. In another embodiment, the catalytic dehydrofluorination is conducted with the temperature set point of the reactor in the range of from about 250° C. to about 300° C. In one embodiment, the contact time is typically from about 1 to about 450 seconds. In another embodiment, the contact time is from about 10 to about 120 seconds.

The reaction pressure can be subatmospheric, atmospheric or superatmostpheric. Generally, near atmospheric pressures are preferred. However, the dehydrofluorination can be beneficially run under reduced pressure (i.e., pressures less than one atmosphere).

In one embodiment, the catalytic dehydrofluorination is carried out in the presence of an inert gas such as nitrogen, helium, or argon. The addition of an inert gas can be used to increase the extent of dehydrofluorination. Of note are processes where the mole ratio of inert gas to hydrofluorocarbon undergoing dehydrofluorination is from about 5:1 to about 0.5:1. In one embodiment, nitrogen is the inert gas.

Reaction product HFC-1234yf and any unconverted HFC-245eb are recovered from the effluent leaving the reactor. The unconverted HFC-245eb can be recycled back to the reactor to produce additional HFC-1234yf. In one embodiment of this invention, the unconverted HFC-245eb is recycled back to the reactor as it's azeotrope with HF. Published PCT Application WO 2008/002501 filed Jun. 27, 2006 and, disclosing an azeotrope of HF/HFC-245eb, is incorporated herein in its entirety. U.S. Pat. No. 7,423,188 discloses an azeotrope of the E-isomer of HFC-1234ze and HF and a method to separate the HFC-1234ze from the azeotrope, and U.S. Pat. No. 7,476,771 discloses an azeotrope of HFC-1234yf and HF and a method to separate the HFC-1234yf from the azeotrope. HFC-1234ze may be recovered as a HF/HFC-1234ze azeotrope. Similarly, HFC-1234yf may be recovered as a HF/HFC-1234yf azeotrope. Pure HFC-1234ze and pure HFC-1234yf can be further recovered from their HF azeotropes by using methods similar to those described in U.S. Pat. No. 7,423,188 and U.S. Pat. No. 7,476,771, and both of which are incorporated herein by reference.

The reactor, or reactor bed, distillation columns, and their associated feed lines, effluent lines, and associated units used in applying the processes of this invention should be constructed of materials resistant to hydrogen fluoride. Typical materials of construction, well-known to the fluorination art, include stainless steels, in particular of the austenitic type, the well-known high nickel alloys, such as Monel™ nickel-copper alloys, Hastelloy™ nickel-based alloys and, Inconel™ nickel-chromium alloys, and copper-clad steel.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Group numbers corresponding to columns within the Periodic Table of the elements use the "New Notation" convention as seen in the *CRC Handbook of Chemistry and Physics*, 81$^{st}$ Edition (2000-2001).

Unless otherwise defined, all technical and scientific terms used herein have the same meaning as commonly understood by one of ordinary skill in the art to which this invention belongs. Although methods and materials similar or equivalent to those described herein can be used in the practice or testing of embodiments of the present invention, suitable methods and materials are described below. All publications, patent applications, patents, and other references mentioned herein are incorporated by reference in their entirety, unless a particular passage is cited. In case of conflict, the present specification, including definitions, will control. In addition, the materials, methods, and examples are illustrative only and not intended to be limiting.

EXAMPLES

The concepts described herein will be further described in the following examples, which do not limit the scope of the invention described in the claims.

In the examples the follow abbreviations or codes may be used:
CT=contact time
1234yf=CF$_3$CF=CH$_2$
245eb=CF$_3$CHFCH$_2$F
1234ze=CF$_3$CH=CHF
245cb=CF$_3$CF$_2$CH$_2$ Example 1

Example 1 demonstrates the dehydrofluorination of 1,1,1,2,3-pentafluoropropane over a chromium oxide catalyst further comprising boron, potassium and sodium.

An inconel tube (⅝ inch OD) was filled with 6 cc (4.9 gm) of hydrated chromic oxide (also known as Guignet's Green) in extrudate form, which was crushed and sieved to 12/20 mesh. A typical analysis of this catalyst indicated the following composition: 54.5% Cr, 1.43% B, 3400 ppm Na, 120 ppm K. The temperature of the catalyst bed was raised to 325° C. and purged with nitrogen (38 sccm, 6.3×10$^{-7}$ m$^3$/sec) for 120 minutes and then at 300° C. for 80 minutes. Then the flow of nitrogen was reduced to 27 sccm (4.5×10$^{-7}$ m$^3$/sec) and HF was fed at 9 sccm (1.5×10$^{-7}$ m$^3$/sec) for 500 minutes. The flow of nitrogen was then lowered to 19 sccm (3.2×10$^{-7}$ m$^3$/sec) and the flow of HF was raised to 15 sccm (2.5×10$^{-7}$ m$^3$/sec) for 25 minutes. The flow of nitrogen was then lowered to 11 sccm (1.8×10$^{-7}$ m$^3$/sec) and the flow of HF was raised to 21 sccm (3.5×10$^{-7}$ m$^3$/sec) for 30 minutes. The flow of nitrogen was then lowered to 4 sccm (6.7×10$^{-8}$ m$^3$/sec) and the flow of HF was raised to 27 sccm (4.5×10$^{-7}$ m$^3$/sec) for 30 minutes. The flow of nitrogen was then discontinued and the flow of HF was raised to 30 sccm (5.0×10$^{-7}$ m$^3$/sec) for 160 minutes. After this activation period, the catalyst bed temperature was changed to reaction conditions.

The reactor temperature was stabilized at temperatures from 250° C. to 302° C., as indicated in the table below, and CF$_3$CHFCH$_2$F was fed at 6.4 sccm (1.1×10$^{-7}$ m$^3$/sec). The CF$_3$CHFCH$_2$F was vaporized at 41° C. while passing nitrogen through the vaporizer at 6.4 sccm (1.1×10$^{-7}$ m$^3$/sec). Part of the reactor effluent was passed through a series of valves and analyzed by GCMS. The results in Table 1 are an average of at least two GC injections at each set of conditions. Amounts for 245 cb and 1234ze are expressed as mole parts per hundred of 2,3,3,3-tetrafluoropropene produced.

TABLE 1

| Mole % 1234yf | 245cb (pph) | 1234ze (pph) | 245eb (%) | Temp ° C. | CT (sec) |
|---|---|---|---|---|---|
| 71.7 | 8.9 | 5.2 | 17.5 | 302 | 28 |
| 47.9 | 6.1 | 4.0 | 46.6 | 275 | 28 |
| 28.9 | 4.5 | 2.8 | 68.4 | 250 | 28 |

Example 2

Example 2 demonstrates the dehydrofluorination of 1,1,1,2,3-pentafluoropropane over chromium oxide catalysts further comprising varying amounts of boron, potassium and sodium.

An inconel tube (½ inch OD) was filled with 6 cc (4.9 gm) of hydrated chromic oxide in extrudate form, which was crushed and sieved to 12/20 mesh. Composition of the catalysts with respect to B, Na and K are as indicated in Table 2. The temperature of the catalyst bed was raised to 300° C. and purged with nitrogen (30 cc/min) for 200 minutes. Then the flow of nitrogen was reduced to 60 cc/min and HF was fed at 20 cc/min for 60 minutes. The temperature was increase to 325° C. for 300 minutes. The flow of nitrogen was then lowered to 30 cc/min and the flow of HF was raised to 30 cc/min for 30 minutes. The flow of nitrogen was then lowered to 12 cc/min and the flow of HF was raised to 48 cc/min for 60 minutes. The flow of nitrogen was then discontinued and the flow of HF was raised to 48 cc/min for 30 minutes. The reactor temperature was then decreased to 250° C. for 30 minutes. Afterwards HF was turned off and the reactor was purged with 30 cc/min of nitrogen. The reactor temperature was then stabilized at 300° C., the flow of nitrogen was turned off, and CF$_3$CHFCH$_2$F was fed at 3.2 ml/hr (12 cc/min). The CF$_3$CHFCH$_2$F was vaporized at 175° C. Part of the reactor effluent was passed through a series of valves and analyzed by GCMS. Amounts for 245 cb and 1234ze are expressed as mole parts per hundred of 2,3,3,3-tetrafluoropropene produced.

TABLE 2

| % B | Na ppm | K ppm | Mole % 1234yf | 245cb (pph) | 1234ze (pph) | 245eb (%) | Temp ° C. | CT (sec) |
|---|---|---|---|---|---|---|---|---|
| 1.1 | 3225 | 135 | 58.1 | 28.5 | 2.7 | 23.20 | 300 | 30 |
| 1.6 | 49 | 17000 | 53.7 | 10.0 | 2 | 39.2 | 300 | 30 |
| 1.6 | 4550 | 150 | 52.8 | 15.5 | 2.9 | 36.68 | 300 | 30 |

Example 3

Example 3 demonstrates the dehydrofluorination of 1,1,1,2,3-pentafluoropropane over chromium oxide catalysts further comprising varying amounts of added potassium.

Chromium oxide catalyst which had a starting composition of 55.8% Cr, 175 ppm Na, 60 ppm K, 53 ppm Cu and 20 ppm Zn was doped with varying levels of potassium. Composition of the catalysts with respect to amount of K added is indicated in Table 3.

An inconel tube (½ inch OD) was filled with 6 cc (4.9 gm) of catalyst which had been prepared as follows. Hydrated chromic oxide in extrudate form, which was crushed and sieved to 12/20 mesh was doped with varying levels of potassium by slurring catalyst with an aqueous potassium carbonate solution containing enough potassium to provide the indicated potassium levels. The solution was then evaporate to dryness, and the resulting catalyst was dried at 200° C. for 3 hours. After charging the reactor tube, the temperature of the catalyst bed was raised to 300° C. and purged with nitrogen (30 cc/min) for 200 minutes. Then the flow of nitrogen was reduced to 60 cc/min and HF was fed at 20 cc/min for 60 minutes. The temperature was increase to 325° C. for 300 minutes. The flow of nitrogen was then lowered to 30 cc/min and the flow of HF was raised to 30 cc/min for 30 minutes. The flow of nitrogen was then lowered to 12 cc/min and the flow of HF was raised to 48 cc/min for 60 minutes. The flow of nitrogen was then discontinued and the flow of HF was raised to 48 cc/min for 30 minutes. The reactor temperature was then decreased to 250° C. for 30 minutes. Afterwards HF was turned off and the reactor was purged with 30 cc/min of nitrogen. The reactor temperature was then stabilized at 300° C., the flow of nitrogen was turned off, and $CF_3CHFCH_2F$ was fed at 3.2 ml/hr (12 cc/min). The $CF_3CHFCH_2F$ was vaporized at 175° C. Part of the reactor effluent was passed through a series of valves and analyzed by GCMS. Amounts for 245cb and 1234ze are expressed as mole parts per hundred of 2,3,3,3-tetrafluoropropene produced.

TABLE 3

| K added - ppm | 1234ze (pph) | 245eb (%) | 1234yf (%) | 245cb (pph) |
|---|---|---|---|---|
| 100 | 12.97 | 9.73 | 31.01 | 45.60 |
| 5000 | 5.30 | 11.83 | 73.4 | 9.47 |
| 6500 | 3.87 | 34.7 | 58.55 | 2.88 |
| 10000 | 0.73 | 82.41 | 16.52 | 0 |

Example 4

Example 3 demonstrates the dehydrofluorination of 1,1,1,2,3-pentafluoropropane over a gamma alumina dehydrofluorination catalyst.

A batch of gamma alumina (BASF) (6 cc, 3.19 gm) was activated as the catalyst in Example 1 described above. The temperature of the reactor was controlled temperatures from 249° C. to 299° C., as indicated in the table below, and $CF_3CHFCH_2F$ was fed at 6.4 sccm ($1.1 \times 10^{-7}$ m³/sec). The $CF_3CHFCH_2F$ was vaporized at 41° C. while passing nitrogen through the vaporizer at 6.4 sccm ($1.1 \times 10^{-7}$ m³/sec). Part of the reactor effluent was passed through a series of valves and analyzed by GCMS. The results in Table 4 are an average of at least two GC injections at each set of conditions. Amounts for 245 cb and 1234ze are expressed as mole parts per hundred of 2,3,3,3-tetrafluoropropene produced.

TABLE 4

| Mole % 1234yf | 245cb (pph) | 1234ze (pph) | 245eb (%) | Temp ° C. | CT (sec) |
|---|---|---|---|---|---|
| 68.7 | 32.5 | 8.0 | 2.9 | 299 | 28 |
| 64.4 | 43.3 | 6.1 | 3.3 | 276 | 28 |
| 57.3 | 46.9 | 3.3 | 13.5 | 249 | 28 |

Example 5

Example 5 demonstrates the dehydrofluorination of 1,1,1,2,3-pentafluoropropane over an alpha chromium oxide catalyst.

A batch of alpha chromium oxide (6 cc, 8.51 gm) as described in U.S. Pat. No. 5,036,036 was activated as the catalyst in Example 1 described above. Analysis of the catalyst indicated the following composition: 55.8% Cr, 0% B, 175 ppm Na, 60 ppm K. The temperature of the reactor was controlled temperatures from 249° C. to 298° C., as indicated in the table below, and $CF_3CHFCH_2F$ was fed at 6.4 sccm ($1.1 \times 10^7$ m³/sec). The $CF_3CHFCH_2F$ was vaporized at 41° C. while passing nitrogen through the vaporizer at 5.4 sccm ($9.5 \times 10^{-8}$ m³/sec). Part of the reactor effluent was passed through a series of valves and analyzed by GCMS. The results in Table 5 are an average of at least two GC injections at each set of conditions. Amounts for 245 cb and 1234ze are expressed as mole parts per hundred of 2,3,3,3-tetrafluoropropene produced.

Analysis of the alpha chromium oxide catalyst indicated it comprised 55.8% chromium, 53 ppm copper, 120 ppm iron, 175 ppm sodium, 60 ppm potassium, 23 ppm manganese, and 20 ppm zinc.

TABLE 5

| Mole % 1234yf | 245cb (pph) | 1234ze (pph) | 245eb (%) | Temp ° C. | CT (sec) |
|---|---|---|---|---|---|
| 65.5 | 34.5 | 11 | 4.1 | 298 | 31 |
| 61.8 | 46.3 | 8.1 | 4.1 | 277 | 31 |
| 57.7 | 59.4 | 5.2 | 4.6 | 249 | 31 |

Example 6

Example 6 demonstrates the dehydrofluorination of 1,1,1,2,3-pentafluoropropane over an chromium oxide gel catalyst.

A batch of chromium oxide gel (6 cc, 7.47 gm) obtained from BASF was activated as the catalyst in Example 1 described above. The temperature of the reactor was controlled temperatures from 249° C. to 298° C., as indicated in the table below, and $CF_3CHFCH_2F$ was fed at 6.4 sccm ($1.1 \times 10^{-7}$ m³/sec). The $CF_3CHFCH_2F$ was vaporized at 41° C. while passing nitrogen through the vaporizer at 5.4 sccm ($9.5 \times 10^{-8}$ m³/sec). Part of the reactor effluent was passed through a series of valves and analyzed by GCMS. The results in Table 6 are an average of at least two GC injections at each set of conditions. Amounts for 245 cb and 1234ze are expressed as mole parts per hundred of 2,3,3,3-tetrafluoropropene produced.

TABLE 6

| Mole % 1234yf | 245cb (pph) | 1234ze (pph) | 245eb (%) | Temp ° C. | CT (sec) |
|---|---|---|---|---|---|
| 69.0 | 33.9 | 6.4 | 1.8 | 299 | 31 |
| 64.4 | 47.0 | 4.0 | 1.5 | 277 | 31 |
| 59.5 | 63.4 | 1.5 | 0.9 | 248 | 31 |

Example 7

Example 7 demonstrates the dehydrofluorination of 1,1,1,2,3-pentafluoropropane over an chromium oxide gel catalyst.

A batch of chromium oxide gel (6 cc, 5.9 gm) obtained from Synetix (CPA200A) was activated as the catalyst in Example 1 described above. The temperature of the reactor was controlled temperatures from 251° C. to 301° C., as indicated in the table below, and $CF_3CHFCH_2F$ was fed at 6.4 sccm ($1.1 \times 10^{-7}$ m$^3$/sec). The $CF_3CHFCH_2F$ was vaporized at 41° C. while passing nitrogen through the vaporizer at 5.4 sccm ($9.5 \times 10^{-8}$ m$^3$/sec). Part of the reactor effluent was passed through a series of valves and analyzed by GCMS. The results in Table 7 are an average of at least two GC injections at each set of conditions. Amounts for 245cb and 1234ze are expressed as mole parts per hundred of 2,3,3,3-tetrafluoropropene produced.

Analysis of the chromium oxide gel catalyst indicated it comprised 62.9% chromium, 350 ppm copper, 198 ppm sodium, 145 ppm iron and 50 ppm potassium.

TABLE 7

| Mole % 1234yf | 245cb (pph) | 1234ze (pph) | 245eb (%) | Temp ° C. | CT (sec) |
|---|---|---|---|---|---|
| 70.8 | 30.5 | 6.2 | 1.8 | 301 | 31 |
| 65.9 | 43.6 | 3.9 | 1.5 | 276 | 31 |
| 67.3 | 42.6 | 1.9 | 1.3 | 251 | 31 |

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is to be appreciated that certain features are, for clarity, described herein in the context of separate embodiments, may also be provided in combination in a single embodiment. Conversely, various features that are, for brevity, described in the context of a single embodiment, may also be provided separately or in any subcombination. Further, reference to values stated in ranges include each and every value within that range.

What is claimed is:

1. A process for the manufacture of 2,3,3,3-tetrafluoropropene comprising: (a) contacting 1,1,1,2,3-pentafluoropropane with a catalyst comprised of chromium (III) oxide and from 0.1% to 2.0% of an alkali metal disposed on the surface of said catalyst, to produce a product mixture comprising 2,3,3,3-tetrafluoropropene and hydrogen fluoride; and (b) recovering said 2,3,3,3-tetrafluoropropene from the product mixture produced in (a).

2. A process of claim 1, wherein said product mixture comprising 2,3,3,3-tetrafluoropropene comprises less than 20 parts per hundred on a molar basis of 1,1,1,2,2-pentafluoropropane.

3. The process of claim 1, wherein said product mixture comprising 2,3,3,3-tetrafluoropropene comprises less than 10 parts per hundred on a molar basis of 1,1,1,2,2-pentafluoropropane.

4. The process of claim 1, wherein said catalyst comprises from 0.1% to 1% alkali metal.

5. The process of claim 1, wherein said catalyst comprises from 0.1% to 1% potassium disposed on the surface of said catalyst.

6. The process of claim 1, wherein said catalyst comprises from 0.1% to 3% boron and at least 3000 ppm of alkali metal.

7. The process of claim 6, wherein said catalyst comprises from 0.5% to 2% boron and at least 3000 ppm of sodium.

8. The process of claim 1, wherein said catalyst comprises from 0.55 to 2% boron and at least 1000 ppm potassium.

9. The process of claim 1, wherein the temperature of the catalyst is maintained at a set point of from 250° C. to 350° C.

10. The process of claim 9, wherein the temperature of the catalyst is maintained at a set point of from 250° C. to 300° C.

11. A process for the manufacture of 2,3,3,3-tetrafluoropropene comprising: (a) contacting 1,1,1,2,3-pentafluoropropane with a catalyst comprised of chromium (III) oxide and from 0.5% to 2.0% of an alkali metal dispersed throughout the particles of said catalyst, to produce a product mixture comprising 2,3,3,3-tetrafluoropropene and hydrogen fluoride; and (b) recovering said 2,3,3,3-tetrafluoropropene from the product mixture produced in (a).

12. The process of claim 11, wherein said product mixture comprising 2,3,3,3-tetrafluoropropene comprises less than 20 parts per hundred on a molar basis of 1,1,1,2,2-pentafluoropropane.

13. The process of claim 11, wherein said product mixture comprising 2,3,3,3-tetrafluoropropene comprises less than 10 parts per hundred on a molar basis of 1,1,1,2,2-pentafluoropropane.

14. The process of claim 11, wherein said catalyst further comprises from 0.1% to 3% boron and at least 3000 ppm of alkali metal.

15. The process of claim 14, wherein said catalyst comprises from 0.5% to 2% boron and at least 3000 ppm of sodium.

16. The process of claim 11, wherein said catalyst comprises from 0.55 to 2% boron and at least 1000 ppm potassium.

17. The process of claim 11, wherein the temperature of the catalyst is maintained at a set point of from 250° C. to 350° C.

18. The process of claim 17, wherein the temperature of the catalyst is maintained at a set point of from 250° C. to 300° C.

* * * * *